United States Patent
McGhie et al.

(10) Patent No.: US 9,757,099 B2
(45) Date of Patent: Sep. 12, 2017

(54) BIOPSY NEEDLE WITH ENHANCED FLEXIBILITY

(71) Applicant: Cook Medical Technologies LLC, Bloomington, IN (US)

(72) Inventors: Thomas McGhie, Bloomington, IN (US); Bryan Chisholm, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 636 days.

(21) Appl. No.: 13/768,086

(22) Filed: Feb. 15, 2013

(65) Prior Publication Data

US 2013/0226030 A1 Aug. 29, 2013

Related U.S. Application Data

(60) Provisional application No. 61/603,705, filed on Feb. 27, 2012.

(51) Int. Cl.
*A61B 10/00* (2006.01)
*A61B 10/02* (2006.01)

(52) U.S. Cl.
CPC .................. *A61B 10/0275* (2013.01)

(58) Field of Classification Search
CPC ............ A61B 10/0275; A61B 10/0266; A61B 2010/0208

(Continued)

(56) References Cited

U.S. PATENT DOCUMENTS

| 4,350,169 A | 9/1982 | Dutcher et al. |
| 5,061,238 A | 10/1991 | Shuler |

(Continued)

FOREIGN PATENT DOCUMENTS

| DE | 10 2004 056 136 A1 | 5/2006 |
| WO | WO 2006/065913 A1 | 6/2006 |

(Continued)

OTHER PUBLICATIONS

Cook Medical, "Variable Injection Needle," Product Description, © 2010, Wilson-Cook Medical, Inc. and Cook Ireland Ltd., 8 pages.

(Continued)

*Primary Examiner* — Daniel Cerioni
(74) *Attorney, Agent, or Firm* — Brinks Gilson & Lione

(57) ABSTRACT

A biopsy stylet and needle system is provided that is configured for navigation and spring-loaded deployment through at least one tortuous or otherwise confined length. The system includes a needle cannula through which a notched biopsy stylet is disposed. The notched biopsy stylet includes at least one outer diameter length that is about the same as, but preferably very slightly less than, the inner diameter of the needle cannula. The notched biopsy stylet also includes at least one outer diameter length that has a smaller diameter, the lengthwise position of which corresponds to the tortuous or otherwise confined length through which the system is to be operated. The smaller stylet diameter length is configured to prevent binding between the stylet and the needle cannula and/or between the needle cannula and an overlying access cannula or other access passage structure.

11 Claims, 3 Drawing Sheets

(58) Field of Classification Search
USPC .......................................................... 600/567
See application file for complete search history.

(56) References Cited

U.S. PATENT DOCUMENTS

| | | | |
|---|---|---|---|
| 6,129,750 A | 10/2000 | Tockman et al. | |
| 6,203,524 B1 | 3/2001 | Burney et al. | |
| 2002/0022788 A1 | 2/2002 | Corvi et al. | |
| 2003/0208136 A1* | 11/2003 | Mark | A61B 10/0275 600/564 |
| 2004/0133124 A1* | 7/2004 | Bates | A61B 10/0275 600/564 |
| 2004/0260199 A1 | 12/2004 | Hardia et al. | |
| 2006/0282100 A1 | 12/2006 | Pasricha et al. | |
| 2007/0106176 A1* | 5/2007 | Mark | A61B 10/0275 600/566 |
| 2009/0177114 A1 | 7/2009 | Chin et al. | |
| 2010/0081965 A1 | 4/2010 | Mugan et al. | |
| 2010/0298736 A1 | 11/2010 | Levy | |
| 2011/0301547 A1* | 12/2011 | Nagase | A61M 5/3213 604/198 |
| 2012/0065543 A1* | 3/2012 | Ireland | A61B 10/0275 600/567 |
| 2012/0179065 A1* | 7/2012 | Ferree | A61B 10/0275 600/567 |
| 2013/0006143 A1* | 1/2013 | Neoh | A61B 10/0275 600/567 |

FOREIGN PATENT DOCUMENTS

| | | |
|---|---|---|
| WO | WO 2008/098241 A1 | 8/2008 |
| WO | WO 2011/053648 A1 | 5/2011 |

OTHER PUBLICATIONS

Robbins Instruments, Inc., Titanium Nitride Scalp Transplant Punches, Product Specification, © 2007, retrieved online Jul. 15, 2010, 2 pages.

* cited by examiner

BIOPSY NEEDLE WITH ENHANCED FLEXIBILITY

CROSS-REFERENCE TO RELATED APPLICATIONS

This application claims priority to U.S. Provisional Patent Application No. 61/603,705, filed Feb. 27, 2012, which is incorporated herein by reference in its entirety.

TECHNICAL FIELD

Embodiments disclosed herein generally relate to medical biopsy devices. More particularly embodiments disclosed related to needle biopsy devices operable through a cannula, endoscope, or other delivery path that may include one or more tortuous portions.

BACKGROUND

Tissue collection devices are configured in a variety of ways to operate in different environments and through different access paths to target tissue. These different operating environments may pose challenges to efficient and effective collection of tissue samples via biopsy. It is generally preferable to acquire biopsied tissue samples in the least invasive, most time-efficient manner. Minimally invasive approaches configured to access internal organs and/or tissues often eschew direct percutaneous access to avoid clinical damage to tissue and/or organs disposed between nearby percutaneous access points. As such, these minimally invasive methods may require navigation through tortuous passages of, for example, a body lumen such as blood vessels or ducts.

Operating a distal tissue-acquisition tool of a biopsy device such as a tray-style (also known as notched) biopsy needle through tortuous passages can impair its functionality. For example, such needle devices may experience binding between a needle body that can cause changes in tool-end affecting hysteresis and may even impair effective extension and retraction of the needle from its sheath. As such, there is a need for biopsy needle devices that provide improved functionality during operation through tortuous access paths.

BRIEF SUMMARY

In one aspect, embodiments disclosed herein may include a notched biopsy needle system having a needle body length with a reduced diameter, as well as methods for using such a device.

In one aspect, embodiments disclosed herein may include a biopsy needle system including an outer access cannula through which a needle cannula is longitudinally disposed. A stylet needle with a notch near its distal end is slidably disposed through a needle cannula lumen. At least one distal portion of the needle stylet between its notch and its distal end includes a first outer diameter that is about the same as, but very slightly less than, the inner diameter of the needle cannula lumen. At least one lengthwise portion of the needle stylet proximal of the notch includes a second outer diameter that is less than the first outer diameter, such that the lower diameter lengthwise portion has greater flexibility than a portion including the first outer diameter and a decreased likelihood of binding if the access cannula incurs a diameter change (e.g., due to curving through a tortuous path).

In certain embodiments, a major length of the needle stylet proximal of the notch may have a diameter less than the first diameter. In other embodiments, the reduced diameter portion may extend along only one or more lengthwise portions of the needle stylet proximal of the notch. In some such embodiments, the reduced diameter portion(s) may be located/configured to correspond to known (or at least to predicted) lengths that have an increased likelihood of binding with the overlying needle cannula during operation.

In some embodiments, the main stylet needle body may have a substantially consistent diameter along its length, which diameter corresponds to the second outer diameter. In such embodiments, a first outer diameter length distal of the notch may be provided by an overlying metallic or polymer ring member secured to the main stylet needle body.

DETAILED DESCRIPTION

Figure 1A:
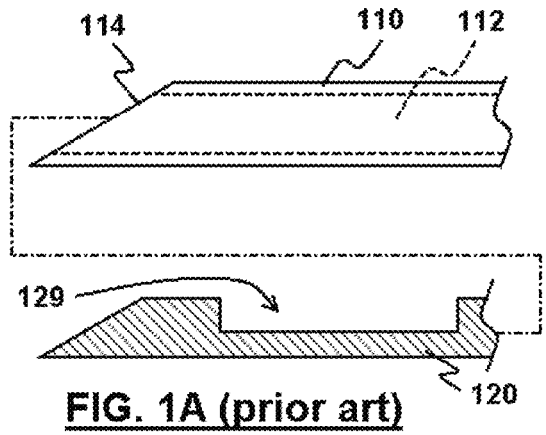
FIGS. 1-1D show a transjugular biopsy procedure.

As used in the specification, the terms proximal and distal should be understood as being from the perspective of a physician performing a procedure (e.g., diagnostic biopsy) upon a patient. Hence the term "distal" means the portion of the delivery system that is farthest from the physician and the term "proximal" means the portion of the device or system that is nearest to the physician. As used herein, the term "outer diameter" refers to the circular diameter defined by a major curve transverse to the longitudinal axis of the cannula, stylet, needle, or other elongate structure. As such the outer diameter is defined as a circle even if the object described as having an outer diameter includes less than a solid circular cross-section (e.g., only a crescent or other partially solid section such as will be present along the notch of a notched stylet).

Embodiments are described with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

Some embodiments of a biopsy needle device are described with reference to a transjugular liver biopsy procedure, already known in the art, for purposes of illustrating advantageous features of the presently-described embodiments. The procedure is described with reference to FIGS. 1-1D, which shows a diagrammatically simplified view of a patient's jugular vein 160, vena cava 162, and hepatic portal vein 164 extending into the liver 166. An access cannula 170 extends through the passage defined by those veins 160, 162, 164 and its distal end is pressed against a wall of the hepatic vein 164 to "tent" it in preparation for penetration by the needle cannula of a target mass 167. The access cannula 170, which may be stainless steel, another alloy, or a stiff polymer, includes a preset curved region 172 configured for transiting from the inferior vena cava into the hepatic portal vein 164.

Figure 1:
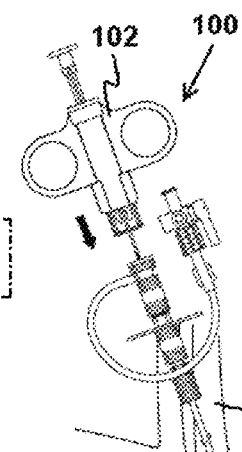
Figure 1B:
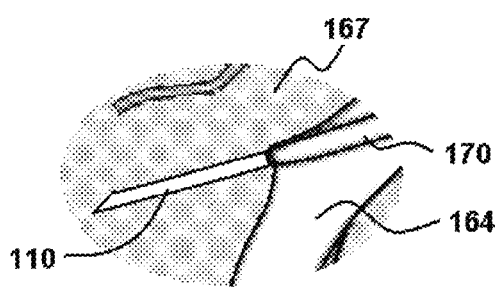

The transjugular liver biopsy procedure is further described with reference to FIGS. 1B-1D, which are detail call-outs of the portion of FIG. 1 outlined by dashed line 1X. As shown in FIG. 1, a spring-loaded biopsy needle device 100 has been directed into lumen of the access cannula 170. This type of device is well-known in the art and, as shown with reference to FIG. 1 and the more detailed disassembled distal detail view of FIG. 1A, it includes a handle 102, an outer needle cannula 110 (shown in FIG. 1B) that defines a longitudinal lumen 112, and a notched needle stylet 120 that extends slidably through the outer cannula lumen. FIG. 1A shows the outer needle cannula 110, which is elongate, generally tubular with a circular cross section, and which has a beveled distal end 114. The stylet 120 also has a circular cross section, and its outer diameter typically is only very slightly less than the inner diameter of the needle cannula lumen 112.

Figure 1C:
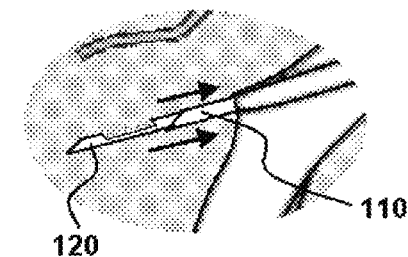
Figure 1D:
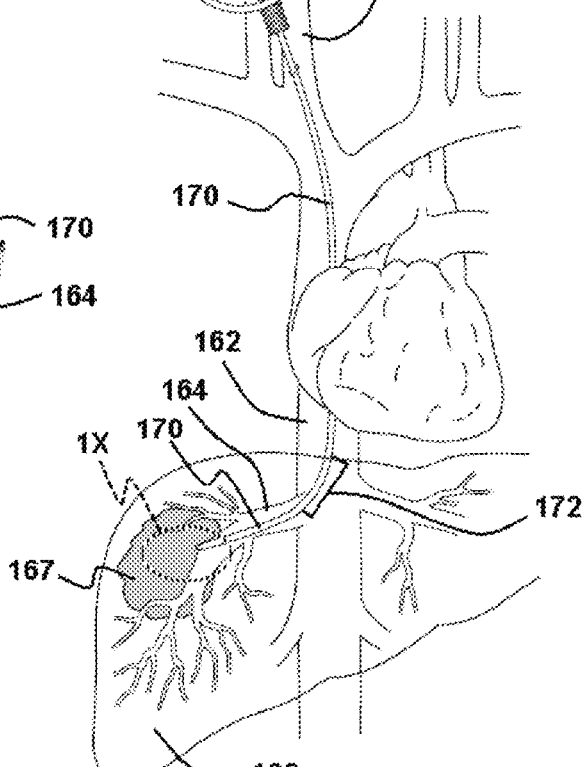
Figure 1D:
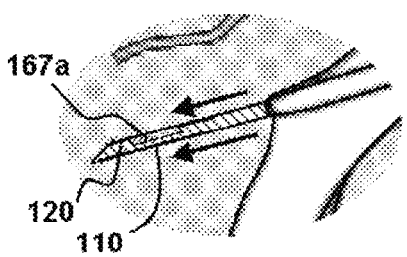

Although operational and structural details vary somewhat between different manufacturers and models, the handle 102 generally includes a spring-loaded mechanism that allows the outer needle cannula 110 to be retracted a discrete distance along the needle stylet 120 sufficient to expose the stylet needle notch 129, as shown in FIG. 1C. In most devices, this loads spring(s) in the handle 102 such that the spring(s) bias the outer needle cannula distally, but its distal advancement to release that load is constrained by a releasable retaining mechanism. As such, this step is referred to as "cocking" the needle.

As shown in FIG. 1B, the outer needle cannula 110 may be advanced through the wall of the hepatic vein 164 into the liver tissue mass 167. Then, as shown in FIG. 1C, the outer needle cannula may be cocked, retracting it proximally from the stylet needle 120 (shown by motion-arrows) and allowing tissue to form thereabout including into the notch 129. Next, the handle 102 may be actuated such that the outer cannula needle 110 is released ("fired") and the spring-bias drives it distally back to its original position overlying the stylet needle 120 (shown by motion-arrows in FIG. 1D). As shown in FIG. 1D (which diagrammatically for illustration purposes shows only the border of the needle cannula 110 and shows the stylet 120 in longitudinal section), this captures a liver tissue biopsy sample 167a in the stylet needle notch 129. The device 100 can then be withdrawn for collection and analysis of the sample 167a.

The preset curved region 172 of the access cannula 170 can present some challenges for effective and efficient operation of the needle device 100. Specifically, the length of a stainless steel (or otherwise constructed) outer needle cannula 110 that traverses the curved region 172 may often have its lumen distorted from a circular section that allows about 0.001 to about 0.002 inches (about 0.0254 to about 0.508 mm) clearance around the inner stylet 120 to an oval section that binds one or more surfaces of the stylet. Stated differently, the very slight difference between the outer diameter of the stylet 120 and the inner diameter of the cannula lumen 112 means that bending and/or curving the cannula 110 increases the likelihood that the circular lumen section will be distorted in a manner contacting and binding the stylet 120. This binding may impair the firing efficiency of the cannula over the stylet such that tissue to be captured is not completely severed within the notch 129, which can result in damage to and/or loss of the sample (e.g., because the sample is still attached to the liver or other target region and gets partially or completely pulled out of the notch 129, damaging the tissue and/or cell structure while the needle device 100 is being withdrawn, some of which may be referred to as "fragmentation"). Friction between the stylet and cannula can result in a bad tissue sample for other reasons, too. The force required to move the cannula distally over the stylet is provided by the spring. If there is too much resistance from binding and bending along the device length, the spring will not even move all the way to the forward (i.e., fully-deployed) position, or it may move very slowly, and result in fragmentation, a small sample, or no sample, as the slowly advancing needle cannula tears and/or pushes tissue out of the way rather than cleanly excising and capturing tissue in the notch 129.

Embodiments described with reference to FIG. 2 and following provide solutions to this problem by providing a reduced diameter length of the stylet needle—particularly along the length of the stylet that it is known will traverse a tight curve or other area likely to experience binding. This may include a stylet length corresponding to—for example—the abovementioned curve of an access cannula for transjugular biopsy, the length of a biopsy needle device that will traverse the distal port of an endoscope working channel during an endoscopic biopsy procedure, or other known or future-developed transit path portions likely to have a curve, turn, or other course-change likely to produce binding between the outer needle cannula and inner stylet.

Figure 2:
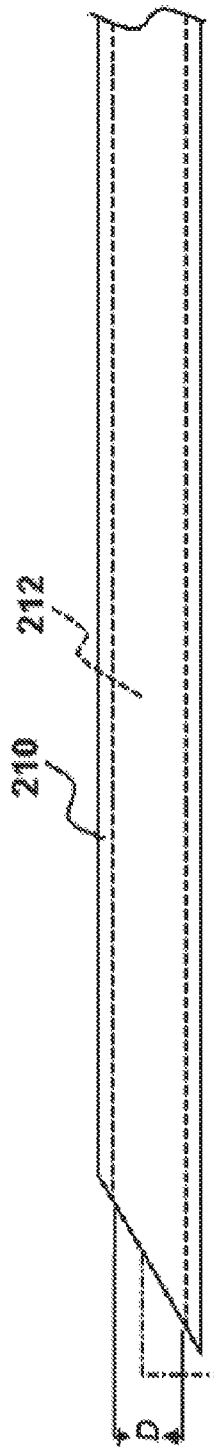
FIG. 2 shows a biopsy needle system embodiment with FIGS. 2A-2D showing transverse section views along lines within FIG. 2 identifying each section view.
Figure 2:
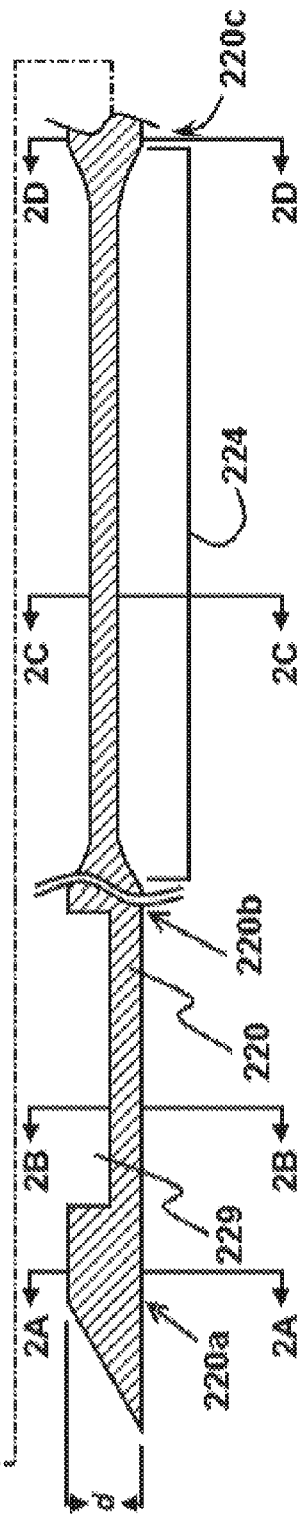
Figure 2:
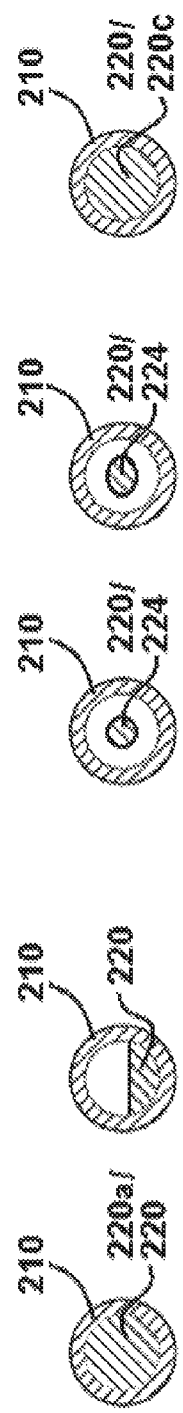

FIG. 2 shows a distal length of an elongate notched biopsy needle stylet 220, slidably disposed through the lumen 212 of a needle cannula 210, with transverse section views shown at FIGS. 2A, 2B, 2C'/2C", and 2D—taken respectively along lines 2A-2A, 2B-2B, 2C-2C, and 2D-2D, which show the stylet 220 as it will appear when disposed within the needle cannula 210 as described above and as indicated by the phantom line of FIG. 2. The stylet 220 is configured with a first outer diameter length 220a immediately distal of the notch 229 (FIG. 2A) and another first outer diameter length 220b (same outer diameter/profile as in FIGS. 2A and 2D) immediately proximal of the notch 229 (FIG. 2B). A second outer diameter length 224 with a reduced outer diameter is more proximal of the notch 229. The second outer diameter length 224 is shown with a smooth transition (as one example, without prejudice to other transition profiles being incorporated in other embodiments) at both ends thereof to the first outer diameter length 220b immediately proximal of the notch 229 and to another first outer diameter length 220c (FIG. 2D) that is still more proximal. The first outer stylet diameter (d in FIG. 2) is about the same or only very slightly less than the needle cannula lumen inner diameter (D in FIG. 2).

The smaller second outer diameter length 224 shown may be formed by centerless grinding of the stylet to reduce its outer diameter along this second outer diameter length 224. Other means of chemically, mechanically, or otherwise reducing circumference may be used. The second outer diameter length 224 may be centered (FIGS. 2C', 2C") or off-center relative to the larger outer diameter of the rest of the stylet 220. However, as shown, it will still have a rounded cross-section (e.g., preferably circular as in FIG. 2C', but may be oval, elliptical as in FIG. 2C", etc.), the outer dimensions of which are smaller than the first outer diameter shown in FIG. 2A. This diameter reduction will provide the second outer diameter length 224 with greater flexibility than the stylet lengths of the first outer diameter (which in this embodiment is a major length of the stylet body) and to prevent interference if the cannula diameter D should partially collapse or become distorted (e.g., "ovalized") due to bending though a curve.

The second outer diameter length 224 preferably will be located a distance proximal of the notch 229 configured to correspond to a known tight curve to be traversed during a procedure. For example, the second outer diameter length 224 may be located along the stylet length of a transjugular biopsy needle device where that device will align with a preset curve of the access cannula. In another example, the second outer diameter length 224 may be located along the stylet length of an endoscopic biopsy needle device where the needle will be tightly curved transiting out of an endoscope working channel at a time and location when the needle is to be fired. This configuration preference will allow both general and device/procedure-specific structure. The preferred location described for the second outer diameter length 224 is that length of a needle device that will transit a binding-likely curve or bend when and where the needle is to be cocked and fired. As such, the lower-diameter/enhanced-flexibility length will prevent or at least reduce the likelihood of binding and will improve the likelihood of desirable sample capture during a needle operation.

In certain embodiments, the second outer diameter length 224 will have an outer diameter that is about 10% to about 50% less than the first outer diameter. For example, an 18-gauge needle device usable through a 14-gauge access cannula may include a needle cannula lumen inner diameter of about 0.041 inches (about 0.104 mm) and a stylet first outer diameter of about 0.040 inches (about 0.102 mm). In a transjugular liver biopsy set, the access cannula may include a preset curve with radii of curvature in the range of about 0.9 to about 2.4 inches along the inner curve of an external access cannula surface, which may increase likelihood of binding in the needle device disposed therethrough. The second outer diameter for a reduced-profile portion of the stylet in keeping with the present disclosure may be, for example, about 0.020 inches (about 0.0508 mm). This description and the other descriptions related to FIG. 2 and its legal equivalents includes that the stylet 220 will be deployed with a biopsy needle system with the stylet disposed through a needle cannula lumen, where that needle cannula, an outer access cannula, and/or an access passage through which the stylet is operated will include a bend or curve corresponding to the smaller diameter length such that the described stylet will provide an operational advantage over a stylet with a larger diameter along that same length.

In various embodiments, different lengths of the stylet 220 may have different diameters. As such, there may be lengths that have a third, fourth, fifth, etc. diameter. Those of skill in the art will appreciate that certain preferred embodiments will include the first outer stylet diameter that is about the same as (although usually very slightly less than) the inner diameter of the needle cannula lumen through which the stylet passes. That first outer stylet diameter most preferably will be included along a stylet length between the notch and the distal end terminus of the stylet. The circular cross section of the reduced diameter length of each of the novel stylet embodiments herein preferably will provide enhanced flexibility along that reduced diameter stylet length. This circular or other round cross section (e.g., including ellipse, oval) preferably will provide generally symmetrical forces when the stylet is navigated through curves, bends, or otherwise tortuous regions and/or decreased likelihood of binding contact, which will minimize likelihood of kinking, bending, or other undesired distortion of the reduced diameter length (e.g., in contrast with a semi-circular or other cross section having one or more corners and/or non-round edges).

Figure 3:
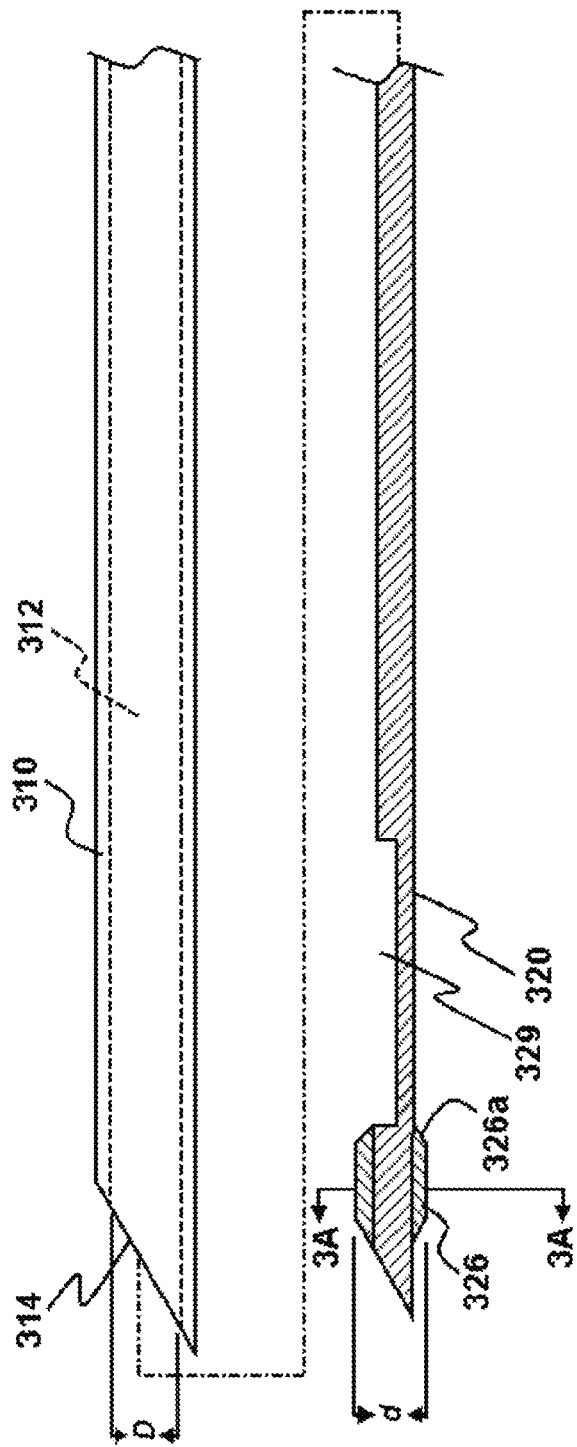
FIGS. 3-3A show another biopsy needle system embodiment.

Another stylet embodiment 320 is described with reference to FIG. 3. This embodiment will include the similar functionality and similar advantages to the embodiment described with respect to FIG. 2. FIG. 3 shows the stylet 320 out of the distal beveled end 314 of a needle cannula 310. Although the needle cannula 310 is shown intact, with its lumen 312 is dashed lines, FIG. 3 shows a longitudinal section view of the stylet 320, which is slidably extendable/retractable from/into the needle cannula lumen 312. The major body length of the stylet 320 includes a second outer diameter that is less than a first outer diameter of a distal ring 326 attached to (or formed integrally with) the stylet body between its notch 329 and its beveled distal end 324.

Figure 3A:

As shown in FIG. 3, the first outer diameter (d) of the distal ring 326 is about the same or only very slightly less than the inner diameter (D) of the needle cannula lumen 312. The second outer diameter of the more proximal length (up to and including substantially all) of the stylet body 320 is less than the first outer diameter (d) and preferably includes a solid circular cross section, as shown in FIG. 3A, which is taken along line 3A-3A of FIG. 3. This difference may be about 10% to about 50% of the first outer diameter. In this embodiment a difference of about 10% to about 20% may be preferred to decrease the likelihood of binding without reducing desirable stiffness for pushability and trackability (and prevent buckling along the length of the device). Some or all of the proximal edge/rim of the ring 326 may be chamfered as shown (326a). The distal chamfering, if present, may be configured to be continuous and/or collinear with the beveling of the stylet end 324. The proximal chamfering, if present, may be configured to transition from the first outer diameter to the distal edge of the notch 329. This reduced diameter along up to a major length of the stylet 320 may provide enhanced flexibility and navigability of a stylet/needle system without sacrificing the functionality of a notched stylet biopsy-collection device.

The first outer diameter ring 326 may be metal alloy (e.g., stainless steel or other) or a—preferably low-friction surface—polymer. The ring may be welded, friction-fit, or secured with adhesive to secure it to the stylet. In some embodiments, the ring 326 may be integrally formed with the stylet body by, for example, tooling, molding, extrusion, or other forming technique(s). Materials useful for the needle and stylet include stainless steel (e.g., for fluoroscopic and/or ultrasound navigation), metal-tipped polymer body biopsy needle construction, and non-ferromagnetic alloys (e.g., NiCr alloys such as Inconel™, which may be MRI-compatible and may also be used in ultrasound navigation if properly configured with dimpling or other echogenicity-enhancing features).

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. For example, a plurality of separate reduced diameter lengths may be provided to provide desired functionality along a path with a corresponding known number and location of tight curves or bends. E.g., for an embodiment including a second outer stylet diameter region of the stylet body proximal of the notch, where the second outer stylet diameter is less than the first outer stylet diameter, a third outer stylet diameter region of the stylet body proximal of the notch and proximal of the second region may be provided, where the third outer stylet diameter also is less than the first outer stylet diameter.

Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:

1. A biopsy needle system, comprising:
    a biopsy needle device comprising:
        a flexible elongate outer needle cannula including
            a proximal cannula end;
            a distal cannula end; and
            a cannula body length therebetween, where the body length includes a needle cannula lumen
                having an inner diameter and
                extending proximally from the distal cannula end; and
        a flexible elongate inner biopsy stylet disposed slidably through at least a portion of the needle cannula lumen, the stylet including
            a proximal stylet end;
            a distal stylet end;
            a generally columnar stylet body therebetween, with at least one distal portion including a first outer diameter of the stylet that is nearly the same as the inner diameter of the needle cannula lumen along at least a first stylet body length;
            a biopsy tissue capture notch along at least one side of the stylet body near the distal stylet end;
            at least one lengthwise portion of the stylet body proximal of the biopsy tissue capture notch, including a second outer diameter of the stylet, where the second outer diameter of the stylet is less than the first outer diameter of the stylet, wherein each of the at least one distal portion and the at least one lengthwise portion of the stylet body are solid in longitudinal cross-section, wherein the at least one lengthwise portion of the stylet body is radially centered relative to the at least one distal portion; and
            where the at least a first stylet body length is between the biopsy tissue capture notch and the distal stylet end; and
        an elongate access cannula through which the needle cannula is disposed, where the elongate access cannula comprises a pre-set curve along at least one lengthwise portion of the stylet body, where the at least one lengthwise portion of the stylet body is disposed a first predetermined distance from the distal stylet end, which first predetermined distance is configured to correspond to alignment of the at least one lengthwise portion of the stylet body with the pre-set curve and to decrease the likelihood of binding between two or more of the access cannula, the biopsy stylet, and the needle cannula.

2. The biopsy needle system of claim 1, where the stylet includes the first outer diameter of the stylet along a second stylet body length immediately adjacent the notch proximal of the biopsy tissue capture notch.

3. The biopsy needle system of claim 2, where the at least one lengthwise portion of the stylet body is disposed proximal of the second stylet body length.

4. The biopsy needle system of claim 1, where the second outer diameter of the stylet is about 10% to about 50% less than the first outer diameter of the stylet.

5. The biopsy needle system of claim 1, where the at least one lengthwise portion of the stylet body proximal of the biopsy tissue capture notch is integral with the stylet body.

6. The biopsy needle system of claim 1, where the needle cannula is spring-biased to have the distal cannula end extend along and past the biopsy tissue capture notch of the stylet.

7. The biopsy needle system of claim 1, where the at least one distal portion includes a ring member with an outermost circumferential dimension secured to the stylet body, and where the first outer diameter of the stylet includes the outermost circumferential dimension of the ring member.

8. The biopsy needle system of claim 7, where at least one edge of the ring member is chamfered.

9. The biopsy needle system of claim 7, where the distal stylet end includes a bevel, where the ring member is immediately adjacent the bevel, and where at least one distal portion of the ring member includes a chamfer that is generally continuous with the bevel.

10. The biopsy needle system of claim 7, where at least one proximal surface of the ring member includes another chamfer.

11. The biopsy needle system of claim 10, where the another chamfer of the at least one proximal surface is generally continuous with the biopsy tissue capture notch.

* * * * *